United States Patent [19]

Taskis

[11] 4,316,886
[45] Feb. 23, 1982

[54] PROCESS FOR THE PREPARATION OF SOLID SODIUM AMOXYCILLIN

[75] Inventor: Charles B. Taskis, Worthing, England

[73] Assignee: Beecham Group Limited, England

[21] Appl. No.: 73,101

[22] Filed: Sep. 6, 1979

[30] Foreign Application Priority Data

Dec. 8, 1978 [GB] United Kingdom ............... 47744/78

[51] Int. Cl.$^3$ ........................ A61K 9/14; A61K 31/43; A61K 31/79
[52] U.S. Cl. ........................................ 424/80; 424/271
[58] Field of Search ................................. 424/80, 271

[56] References Cited

U.S. PATENT DOCUMENTS

| | | | |
|---|---|---|---|
| 3,634,586 | 1/1972 | Kaser et al. | 424/80 |
| 3,928,566 | 12/1975 | Briggs et al. | 424/271 X |
| 3,932,615 | 1/1976 | Ito et al. | 424/80 |
| 4,018,889 | 4/1977 | Armstrong | 424/80 |
| 4,024,240 | 5/1977 | Thakkar | 424/80 |
| 4,029,804 | 6/1977 | Clark et al. | 424/271 |

*Primary Examiner*—Natalie Trousof
*Assistant Examiner*—Vera C. Clarke
*Attorney, Agent, or Firm*—Jacobs & Jacobs

[57] ABSTRACT

Sodium amoxycillin suitable for injection may be prepared by removing the solvent from a solution of sodium amoxycillin and polyvinylpyrrolidone.

14 Claims, No Drawings

PROCESS FOR THE PREPARATION OF SOLID SODIUM AMOXYCILLIN

This invention relates to a process for the preparation of sodium amoxycillin.

British Pat. No. 1,241,844 discloses inter alia amoxycillin and its salts. Amoxycillin, which is the penicillin of the formula:

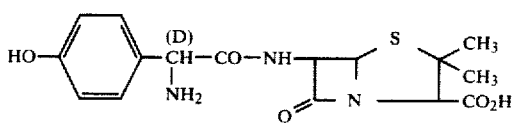

is widely recognised as having a broad spectrum of antibacterial activity of a high order. One of amoxycillin's great advantages is that it is very well absorbed after oral administration but there are occasions when it is desirable to administer it parenterally. It is possible to use the methods disclosed in British Pat. No. 1,241,844 to prepare sodium amoxycillin which may then be dissolved in sterile, pyrogen-free water and used as an injectable composition. However, the previously disclosed process for the preparation of sodium amoxycillin tends to give somewhat poor results in terms of yield and purity. These disadvantages have not prevented the use of the known process for preparing the salt for use in injectable compositions but clearly it would be advantageous to have a process available that led to good yields of a purer product that has improved stability and appearance on reconstitution.

One such improved process is described in our West German Offenlegungsschrift No. 2734622 in which process a solution of sodium amoxycillin in aqueous isopropyl alcohol is spray dried. The product of this process may be reconstituted in water to yield a solution of good stability and appearance.

Another such improved process is described in our U.K. Pat. No. 1527557, in which process a solution of sodium amoxycillin in a solvent system which contains water and a secondary or tertiary carbinol of 4 to 5 carbon atoms (such as tert-butanol) is freeze dried.

We have now discovered a further improved process for preparing sodium amoxycillin which produces a particularly pure product and which in a preferred embodiment dispenses with the need to use an organic solvent in the preparative solution as in the processes of West German Offenlegungsschrift No. 2734622 and U.K. Pat. No. 1527557. This process also has further advantages which will become clear from the following description.

Accordingly the present invention provides a process for the preparation of a solid sodium amoxycillin which process comprises removing the solvent from an aqueous solution of sodium amoxycillin and polyvinyl pyrrolidone of molecular weight from 1000 to 12000.

What is meant herein by an "aqueous solvent" is water or water in homogeneous mixture with one or more organic solvents. Favoured organic solvents of this kind include the lower (C$_{1-4}$) alkanols such as methanol, ethanol and isopropanol. Such organic solvents when present will not comprise more than 50% v/v of the mixture, more suitably not more than 35% v/v of the mixture, favourably not more than 25% v/v of the mixture and preferably not more than 20% v/v of the mixture. Indeed it is one of the considerable advantages of this invention that it can dispense with the presence of such organic solvents if desired which represents a considerable saving in cost and is generally much more convenient since it avoids the necessity of solvent recovery and eliminates the need for the extra precautions required when vaporising flammable materials.

Thus in a favoured aspect this invention provides a process for the preparation of solid amoxycillin which process comprises removing the water from a solution in water of sodium amoxycillin and polyvinylpyrrolidone having a molecular weight from 1000 to 12000.

The polyvinylpyrrolidone (hereafter referred to as PVP) used in the process of this invention will have a molecular weight of from 1000 to 12000. Since the material is a polymer it will be realised by a chemist that the molecular weight referred to is an average molecular weight. A suitable method of determining the average molecular weight of PVP for use in the process of this invention is gel permeation chromatography. The PVP should not contain molecules with a molecular weight of more than 30,000. Similarly it should not have a monomer content of more than 1%. The K value of suitable PVP will generally be between 10 and 18.

Favourably the PVP employed will have a molecular weight of 1500 to 6000.

A preferred PVP for use in the process of this invention will have a molecular weight of 2000–3500. A PVP of this kind is Kollidon CE 5080 (Kollidon is a Registered Trade Mark) which is available from BASF Aktiengesellschaft, D-6700 Ludwigshafen; Federal Republic of Germany. This PVP has a K value of 12 to 14 which is a favoured range.

The starting solution employed (that is the solution from which the solvent is removed) in the process of this invention will generally contain from 2% to 20% w/v of sodium amoxycillin, favourably from 5% w/v to 15% w/v of sodium amoxycillin and preferably from 6% w/v to 12% w/v of sodium amoxycillin.

The starting solution employed in the process of this invention will generally contain from 5% to 40% w/v of PVP, favourably from 5% w/v to 30% w/v of PVP and preferably from 10% w/v to 20% w/v of PVP.

The ratio of sodium amoxycillin to PVP employed may vary widely but in general it is between 1:0.1 and 1:3 favourably from 1:0.2 to 1:1.4 and preferably from 1:0.4 to 1:1.25.

In general if the starting solutions employed in the process of this invention are to be held for any extended period they are most suitably chilled, for example to below 5° C. and more suitably not above 0° C.

Any particulate matter which may form during this chilling or holding stage should be removed by filtration prior to removal of the solvent.

It is one of the advantages of the process of this invention that the starting solutions employed may be held for a longer period than those used in previously known processes such as that of West German Offenlegungsschrift No. 2734622 which is an additional convenience for large scale manufacture.

In one preferred embodiment of this invention the solvent may be removed from the aqueous solution by spray drying. In this embodiment the spray drying may be carried out in conventional manner, for example under conditions as described in West German Offenlegungsschrift No. 2734622.

In a further preferred embodiment of this invention the solvent may be removed from the aqueous solution by freeze drying. The freeze drying may be carried out in bulk or in solution already in vials (or similar containers) which may be sealed after drying. Suitable freeze drying techniques are described in U.K. Pat. No. 1527557.

The starting solution may be prepared in any convenient manner such as dissolving PVP in a solution of sodium amoxycillin or by forming sodium amoxycillin in a solution of PVP by adding sufficient of a sodium base to a suspension of amoxycillin trihydrate in a solution of PVP to cause dissolution of the antibiotic. Suitable methods of dissolving amoxycillin trihydrate in this manner are described in West German Offenlegungsschrift No. 2734622.

If desired small amounts of antioxidants such as sodium metabisulphite may be employed to reduce any tendency to discolouration of the PVP.

The solutions adapted to be dried also form part of this invention. Thus the present invention provides a solution having a volume from 1:1 to 1000:1 which comprises sodium amoxycillin and polyvinylpyrrolidone having a molecular weight of from 1000 to 12000 dissolved in an aqueous solvent.

Aptly the solution is adapted as previously described herein.

The following Examples illustrate the invention. Except where otherwise stated the sodium amoxycillin was prepared by the process of West German Offenlegungsschrift No. 2734622.

The product of the process of this invention has the further advantage that it does not discolour in the manner of the product of previously known processes.

EXAMPLE 1

(Freeze drying)

An aqueous solution containing 7.5% w/v PVP (Kollidon 12 PF) and 6.25% sodium amoxycillin was prepared. 4 ml. quantities were filled into suitable vials (5 or 10 ml) and frozen at −40° C. for 2 hours. The chamber was then exposed to vacuum and the shelf temperature allowed to rise to 0° C. over 14 hours, with the vacuum controlled at 10⁻¹ torr. The shelf temperature was then raised to +40° over 1 hour and held for a further 3 hours. Total Cycle Time=20 hours.

The product was reconstituted in water (1.5 ml) to give a 15% PVP solution containing sodium amoxycillin (equivalent to 250 mg amoxycillin in 2 ml.

EXAMPLE 2

Amoxycillin trihydrate (33.75 g) and PVP Kollidon 12 PF (56.25 g) were stirred with water (300 ml) using a Silverson homogenizer (a vortex stirrer). This solution was titrated with 2 N sodium hydroxide (40.5 ml) to give a clear solution (pH 8.80) containing equimolar quantities of amoxycillin and sodium. The solution volume was made up to 450 ml. 4 ml samples of the final solution containing 6.25% sodium amoxycillin and 12.5% PVP were filled into vials and frozen for 3 hours at −40° C.

The chamber was then exposed to vacuum and the following cycle undertaken.

| Temperature raised to | −20° C. over 1½ hr. |
| Retained at | −20° C. over 5 hr. |
| Allowed to rise to | 0° C. over 6 hr. |
| Allowed to rise to | +10° C. over 2 hr. |
| Heated to | +20° C. over 1 hr. |
| Heated to | +40° C. over 1 hr. |
| Temperature held at | +40° C. for 3 hr. |
| Total cycle time = 22 hours. | |

The product was reconstituted in water (1.5 ml) to give a 25% PVP solution containing sodium amoxycillin (equivalent to 250 gm amoxycillin) in 2 ml.

EXAMPLE 3

A solution containing sodium amoxycillin (equivalent to 6.5% amoxycillin) and 5% w/v PVP (Kollidon 12 PF) was spray dried on small glass spray dryer (Lab. Plant Ltd.) to give a fine white powder product.

| Conditions: | | | |
|---|---|---|---|
| Inlet Air Temp. | = 200° C. | Cooling Air Flow | = 40 L/min |
| Exhaust Temp. | = 86° C. | Pump Flow Rate | = 6.4 ml/min |
| Atomizer | | Atomizer | |
| Air Flow | = 50 L/min. | Head Diam. | = 0.75 mm. |

510 mg of this product was reconstituted in water (1.5 ml) to give a clear solution (10% w/v PVP) containing sodium amoxycillin (equivalent to 250 mg amoxycillin) in 2 ml.

EXAMPLE 4

A solution containing 6% w/v sodium amoxycillin (5% w/v p.f.a.) and 12% PVP (Kollidon 12 PF) was spray dried in the small glass spray dryer. A fine white powdered product was obtained.

| Conditions: | | | |
|---|---|---|---|
| Inlet Temp. | = 180° C. | Cooling Air Flow | = 40 L/min |
| Exhaust Temp. | = 80° C. | Pump Flow Rate | = 6.4 ml/min |
| Atomizer | | Atomizer | |
| Air Flow | = 55 L/min | Head Diam. | = 0.75 mm. |

800 mg of product was reconstituted in water (1.5 ml) to give a clear solution containing 25% PVP sodium amoxycillin (equivalent to 250 mg amoxycillin) in 2 ml.

What we claim is:

1. A process for the preparation of a solid sodium amoxycillin which process comprises removing the solvent from an aqueous solution of sodium amoxycillin containing from 2% to 20% w/v of the sodium amoxycillin and polyvinylpyrrolidone of molecular weight from 1000 to 12000.

2. A process as claimed in claim 1 wherein the polyvinylpyrrolidone has a molecular weight from 1500 to 6000.

3. A process as claimed in claim 1 wherein the polyvinylpyrrolidone has a molecular weight of 2000 to 3500.

4. A process as claimed in claim 1 wherein the starting solution contains 5% w/w to 15% w/w of sodium amoxycillin.

5. A process as claimed in claim 4 wherein the starting solution contains 6% w/v to 12% w/v of sodium amoxycillin.

6. A process as claimed in claim 5 wherein the starting solution contains 10% w/v to 20% w/v of polyvinylpyrrolidone.

7. A process as claimed in claim 1 wherein the weight ratio of sodium amoxycillin to polyvinylpyrrolidone is from 1.04 to 1.125.

8. A process as claimed in claim 1 wherein the starting solution is chilled to below 5° C. and filtered prior to removal of solvent.

9. A process as claimed in claim 1 wherein the solvent is removed by spray drying.

10. A process as claimed in claim 1 wherein the solvent is removed by freeze drying.

11. A process as claimed in claim 1 wherein the starting solution has been formed by dissolving the polyvinylpyrrolidone in an aqueous solution of sodium amoxycillin.

12. A process as claimed in claim 1 wherein the starting solution has been formed by adding sodium hydroxide to a suspension of amoxycillin trihydrate in a solution of polyvinylpyrrolidone.

13. Solid sodium amoxycillin of increase purity and improved stability and appearance for reconstitution for injection and obtained by removing the solvent from a solution of sodium amoxycillin in water and from 5% to 40% w/v polyvinylpyrrolidone of 1000 to 12000 molecular weight by spray drying or freeze drying, the said sodium amoxicillin before reconstitution and solvent removal containing a proportionate amount of the polyvinylpyrrolidone.

14. A solution of sodium amoxycillin adapted to be dried to form the solid sodium amoxycillin of claim 13, which solution comprises sodium amoxycillin and polyvinylpyrrolidone of 1000 to 12000 molecular weight dissolved in an aqueous solvent.

* * * * *